United States Patent [19]

Keaschall

[11] Patent Number: 5,506,367
[45] Date of Patent: Apr. 9, 1996

[54] INBRED CORN LINE PHP38

[75] Inventor: Joseph W. Keaschall, Sharpsville, Ind.

[73] Assignee: Pioneer Hi-Bred International, Inc., Des Moines, Iowa

[21] Appl. No.: 996,378

[22] Filed: Dec. 23, 1992

Related U.S. Application Data

[63] Continuation-in-part of Ser. No. 542,364, Jun. 20, 1990, abandoned.

[51] Int. Cl.$^6$ .............................. A01H 5/00; A01H 11/00; C12H 5/04
[52] U.S. Cl. .................. 800/200; 800/250; 800/DIG. 56; 435/240.4; 435/240.45; 435/240.49
[58] Field of Search ..................................... 800/200, 250, 800/DIG. 56; 47/58.03, 58.05; 435/172.2, 240.4, 240.85, 240.49

[56] References Cited

PUBLICATIONS

Phillips et al. (1988) Cell/Tissue Culture and In Vitro Manipulation: In corn & corn Improvement. Ed. Spragur et al. pp. 345–387.

Primary Examiner—Gary Benzion
Attorney, Agent, or Firm—Michael J. Roth; Nina L. Pearlmutter

[57] ABSTRACT

According to the invention, there is provided an inbred corn line, designated PHP38. This invention thus relates to the plants and seeds of inbred corn line PHP38 and to methods for producing a corn plant produced by crossing the inbred line PHP38 with itself or with another corn plant. This invention further relates to hybrid corn seeds and plants produced by crossing the inbred line PHP38 with another corn line or plant and to crosses with related species.

6 Claims, No Drawings

INBRED CORN LINE PHP38

This is a continuation-in-part of application Ser. No. 07/542,364 filed on Jun. 20, 1990 now abandoned.

FIELD OF THE INVENTION

This invention is in the field of corn breeding, specifically relating to an inbred corn line designated PHP38.

BACKGROUND OF THE INVENTION

The goal of plant breeding is to combine in a single variety/hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produce a uniform population of hybrid plants that may be heterozygous for many gene loci. A cross of two plants each heterozygous at a number of gene loci will produce a population of hybrid plants that differ genetically and will not be uniform.

Corn plants (*Zea mays* L.) can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the incipient ears.

The development of corn hybrids requires the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other broad-based sources into breeding pools from which new inbred lines are developed by selfing and selection of desired phenotypes. The new inbreds are crossed with other inbred lines and the hybrids from these crosses are evaluated to determine which of those have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_5$, etc.

Backcrossing can be used to improve an inbred line. Backcrossing transfers a specific desirable trait from one inbred or source to an inbred that lacks that trait. This can be accomplished for example by first crossing a superior inbred (A) (recurrent parent) to a donor inbred (non-recurrent parent), which carries the appropriate gene(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

A single cross hybrid corn variety is the cross of two inbred lines, each of which has a genotype which complements the genotype of the other. The hybrid progeny of the first generation is designated $F_1$. In the development of hybrids only the $F_1$ hybrid plants are sought. Preferred F hybrids are more vigorous than their inbred parents. This hybrid vigor, or heterosis, can be manifested in many polygenic traits, including increased vegetative growth and increased yield.

The development of a hybrid corn variety involves three steps: (1) the selection of plants from various germplasm pools; (2) the selfing of the selected plants for several generations to produce a series of inbred lines, which, although different from each other, each breed true and are highly uniform; and (3) crossing the selected inbred lines with unrelated inbred lines to produce the hybrid progeny ($F_1$). During the inbreeding process in corn, the vigor of the lines decreases. Vigor is restored when two unrelated inbred lines are crossed to produce the hybrid progeny ($F_1$). An important consequence of the homozygosity and homogeneity of the inbred lines is that the hybrid between any two inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid is produced from four inbred lines crossed in pairs (A×B and C×D) and then the two $F_1$ hybrids are crossed again (A×B)× (C×D). Much of the hybrid vigor exhibited by $F_1$ hybrids is lost in the next generation ($F_2$). Consequently, seed from hybrid varieties is not used for planting stock.

Corn is an important and valuable field crop. Thus, a continuing goal of plant breeders is to develop high-yielding corn hybrids that are agronomically sound based on stable inbred lines. The reasons for this goal are obvious: to maximize the amount of grain produced with the inputs used and minimize susceptibility to environmental stresses. To accomplish this goal, the corn breeder must select and develop superior inbred parental lines for producing hybrids. This requires identification and selection of genetically unique individuals which in a segregating population occur as the result of a combination of crossover events plus the independent assortment of specific combinations of alleles at many gene loci which results in specific genotypes. Based on the number of segregating genes, the frequency of occurrence of an individual with a specific genotype is less than 1 in 10,000. Thus, even if the entire genotype of the parents has been characterized and the desired genotype is known, only a few if any individuals having the desired genotype may be found in a large $F_2$ or $S_0$ population.

Typically, however, the genotype of neither the parents nor the desired genotype is known in any detail.

SUMMARY OF THE INVENTION

According to the invention, there is provided a novel inbred corn line, designated PHP38. This invention thus relates to the seeds of inbred corn line PHP38, to the plants of inbred corn line PHP38, and to methods for producing a corn plant produced by crossing the inbred line PHP38 with itself or another corn line. This invention further relates to hybrid corn seeds and plants produced by crossing the inbred line PHP38 with another corn line or a related species.

DEFINITIONS

In the description and examples that follow, a number of terms are used herein. In order to provide a clear and consistent understanding of the specification and claims, including the scope to be given such terms, the following definitions are provided:

ABS=absolute measurement and % MN is percentage of mean of the experiments in which inbread or hybrid was grown unless otherwise defined.

BAR PLT=BARREN PLANTS. This is the percent of plants per plot that were not barren (lack ears).

BRT STK=BRITTLE STALKS. This is a measure of the stalk breakage near the time of pollination, and is an indication of whether a hybrid or inbred would snap or break near the time of flowering under severe winds. Data are presented as percentage of plants that did not snap.

BU ACR=YIELD (BUSHELS/ACRE). Actual yield of the grain at harvest adjusted to 15.5% moisture. ABS is in absolute terms and % MN is percent of the means for the experiments in which the inbred or hybrid was grown.

CLD TST=COLD TEST. This is the percentage of kernels that germinate under cold soil conditions.

COB SC=COB SCORE. The cob score is a rating of how well the grain is shelled off the cob and how badly the cob is broken up going through the combine. This is given as a 1 to 9 score with 9 being very good. A high score indicates that the grain shells off of the cob well, and the cob does not break.

DRP EAR=DROPPED EARS. This is a measure of the number of dropped ears per plot and represents the percentage of plants that did not drop ears prior to harvest.

EAR HT=EAR HEIGHT. The ear height is a measure from the ground to the top developed ear node attachment and is measured in inches.

EAR SZ=EAR SIZE. A 1 to 9 visual rating of ear size. The higher the rating the larger the ear size.

EST CNT=EARLY STAND COUNT. This is a measure of the stand establishment in the spring and represents the number of plants that emerge on a per plot basis for the inbred or hybrid.

GDU SHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp})}{2} - 50$$

The highest maximum temperature used is 86° F. and the lowest minimum temperature used is 50° F. For each inbred or hybrid it takes a certain number of GDUs to reach various stages of plant development.

GDU SLK=GDU TO SILK. The number of growing degree units required for an inbred line or hybrid to have approximately 50 percent of the plants with silk emergence from time of planting. Growing degree units are calculated by the Barger Method as given in GDU SHD definition.

GRN QUL=GRAIN QUALITY. This is a 1 to 9 rating for the general quality of the shelled grain as it is harvested based on such factors as the color of the harvested grain, any mold on the grain, and any cracked grain. High scores indicate good grain quality.

MST=HARVEST MOISTURE. The moisture is the actual percentage moisture of the grain at harvest.

PLT HT=PLANT HEIGHT. This is a measure of the height of the plant from the ground to the tip of the tassel in inches.

POL SC=POLLEN SCORE. A 1 to 9 visual rating indicating the amount of pollen shed. The higher the score the more pollen shed.

PRM=PREDICTED RM. This trait, predicted relative maturity (RM), is based on the harvest moisture of the grain. The relative maturity rating is based on a known set of checks and utilizes standard linear regression analyses and is referred to as the Minnesota Relative Maturity Rating System.

RT LDG=ROOT LODGING. Root lodging is the percentage of plants that do not root lodge; plants that lean from the vertical axis at an approximately 30° angle or greater would be counted as root lodged.

SCT GRN=SCATTER GRAIN. A 1 to 9 visual rating indicating the amount of scatter grain (lack of pollination or kernel abortion) on the ear. The higher the score the less scatter grain.

SDG VGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A corn breeder may utilize his or her own set of traits for the selection index. One of the traits that is almost always included is yield. The selection index data presented in the tables represent the mean value averaged across testing stations.

STA GRN=STAY GREEN. Stay green is the measure of plant health near the time of black layer formation (physiological maturity). A high score indicates better late-season plant health.

STK CNT=NUMBER OF PLANTS. This is the final stand or number of plants per plot.

STK LDG=STALK LODGING. This is the percentage of plants that did not stalk lodge (stalk breakage) as measured by either natural lodging or pushing the stalks and determining the percentage of plants that break below the ear.

TAS BLS=TASSEL BLAST. A 1 to 9 visual rating was used to measure the degree of blasting (necrosis due to heat stress) of the tassel at time of flowering. A 1 would indicate a very high level of blasting at time of flowering, while a 9 would have no tassel blasting.

TAS SZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TEX EAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER=TILLERS. A count of the number of tillers per plot that could possibly shed pollen was taken. Data is given as percentage of tillers: number of tillers per plot divided by number of plants per plot.

TST WT=TEST WEIGHT UNADJUSTED. The measure of the weight of the grain in pounds for a given volume (bushel).

TST WTA=TEST WEIGHT ADJUSTED. The measure of the weight of the grain in pounds for a given volume (bushel) adjusted for percent moisture.

YLD=YIELD. It is the same as BU ACR ABS.

YLD SC=YIELD SCORE. A 1 to 9 visual rating was used to give a relative rating for yield based on plot ear piles. The higher the rating the greater visual yield appearance.

MDM CPX=Maize Dwarf Mosaic Complex (MDMV= Maize Dwarf Mosaic Virus & MCDV=Maize Chlorotic Dwarf Virus): Visual rating (1–9 score) where a "1" is very susceptible and a "9" is very resistant.

COM SMT=Common Smut (*Ustilago maydis*): Percentage of plants that did not have infection.

SLF BLT Southern Leaf Blight (*Bipolaris maydis, Helminthosporium maydis*): Visual rating (1–9 score) where a "1" is very susceptible and a "9" is very resistant.

NLF BLT=Northern Leaf Blight (*Exserohilum turcicum, H. turcicum*): Visual rating (1–9 score) where a "1" is very susceptible and a "9" is very resistant.

COM RST=Common Rust (*Puccinia sorghi*): Visual rating (1–9 score) where a "1" is very susceptible and a "9" is very resistant.

EYE SPT=Eyespot (*Kabatiella zeae*): Visual rating (1–9 score) where a "1" is very susceptible and a "9" is very resistant.

GLF SPT=Gray Leaf Spot (*Cercospora zeae-maydis*): Visual rating (1–9 score) where a "1" is very susceptible and a "9" is very resistant.

STW WLT=Stewart's Wilt (*Erwinia stewartii*): Visual rating (1–9 score) where a "1" is very susceptible and a "9" is very resistant.

HD SMT=Head Smut (*Sphacelotheca reliana*): Percentage of plants that did not have infection.

EAR MLD=General Ear Mold: Visual rating (1–9 score) where a "1" is very susceptible and a "9" is very resistant. This is based on overall rating for ear mold of mature ears without determining specific mold organism, and may not be predictive for a specific ear mold.

ECB DPE=Dropped ears due to European Corn Borer (*Ostrinia nubilalis*): Percentage of plants that did not drop ears under second brood corn borer infestation.

ECB 2SC=European Corn Borer Second Brood (*Ostrinia nubilalis*): Visual rating (1–9 score) of post flowering damage due to infestation by European Corn Borer. A "1" is very susceptible and a "9" is very resistant.

ECB 1LF=European Corn Borer First Brood (*Ostrinia nubilalis*): Visual rating (1–9 score) of pre-flowering leaf feeding by European Corn Borer. A "1" is very susceptible and a "9" is very resistant.

DETAILED DESCRIPTION OF THE INVENTION

Inbred corn line PHP38 is a yellow, dent corn inbred that provides an acceptable male or female parental line in crosses for producing first generation F1 corn hybrids. PHP38 is best adapted to the central and eastern regions of the united States. Hybrids of PHP38 also possess very good drought tolerance and stability of yield which makes them extremely well-adapted for the hot, arid growing areas of the Western United States. The inbred can be used to produce hybrids from approximately 111–126 relative maturity based on the Minnesota Relative Maturity Rating System for harvest moisture of grain. PHP38 should make a good female since it has acceptable yield, good early vigor, and good early stand establishment. PHP38 would also be acceptable as a male because of its pollen yield. The inbred in hybrid combination has excellent stay green and overall disease tolerance. PHP38 has excellent stalks and above average roots. PHP38 hybrids generally have very good grain quality and high test weight.

The inbred has shown uniformity and stability within the limits of environmental influence for all the traits as described in the Variety Description Information (Table 1) that follows. Most of the data in the Variety Description Information was collected at Johnston, Iowa. The inbred has been self-pollinated and ear-rowed a sufficient number of generations with careful attention paid to uniformity of plant type to ensure homozygousity and phenotypic stability. The line has been increased both by hand and in isolated fields with continued observation for uniformity. No variant traits have been observed or are expected in PHP38.

Inbred corn line PHP38, being substantially homozygous, can be reproduced by planting seeds of the line, growing the resulting corn plants under self-pollinating or sib-pollinating conditions with adequate isolation, and harvesting the resulting seed, using techniques familiar to the agricultural arts.

TABLE 1

VARIETY DESCRIPTION INFORMATION
INBRED = PHP38

| Type: Dent | Region Best Adapted: Central & Eastern Corn Belt |
|---|---|
| A. Maturity: Average across maturity zones. Zone: 0 | |
| Heat Unit Shed: | 1480 |
| Heat Unit Silk: | 1500 |
| No. Reps: | 64 |

TABLE 1-continued

VARIETY DESCRIPTION INFORMATION
INBRED = PHP38

$$\text{HEAT UNITS} = \frac{[\text{Max. Temp. } (\leq 86° \text{ F.}) + \text{Min. Temp } (\geq 50° \text{ F.})]*}{2} - 50$$

B. Plant Characteristics:

| | |
|---|---|
| Plant height (to tassel tip): | 225 cm |
| Length of top ear internode: | 12 cm |
| Number of ears per stalk: | Single |
| Ear height (to base of top ear): | 82 cm |
| Number of tillers: | None |
| Cytoplasm type: | Normal |

C. Leaf:

| | |
|---|---|
| Color: | (B14) Dark Green |
| Angle from Stalk: | <30 degrees |
| Marginal Waves: | (WF9) Few |
| Number of Leaves (mature plants): | 20 |
| Sheath Pubescence: | (W22) Light |
| Longitudinal Creases: | (PA11) many |
| Length (Ear node leaf): | 80 cm |
| Width (widest point, ear node leaf): | 9 cm |

D. Tassel:

| | |
|---|---|
| Number lateral branches: | 8 |
| Branch Angle from central spike: | >45 degrees |
| Pollen Shed: | Medium based on Pollen yield test (98% of experiement means) |
| Peduncle Length (top leaf to basal branches): | 22 cm |
| Anther Color: | Red |
| Glume Color: | Green |

E. Ear (Husked Ear Data Except When Stated Otherwise):

| | |
|---|---|
| Length: | 16 cm |
| Weight: | 121 gm |
| Mid-point Diameter: | 45 mm |
| Silk Color: | Yellow |
| Husk Extension (Harvest stage): | (>10 cm) Very long |
| Husk Leaf: | (8–15 cm) Medium |
| Taper of Ear: | Average |
| Position of Shank (dry husks): | Pendent |
| Kernel Rows: | Straight, Distinct Number = 16 |
| Husk Color (fresh): | Light green |
| Husk Color (dry): | Buff |
| Shank Length: | 13 cm |
| Shank (No. of internodes): | 8 |

F. Kernel (Dried):

Size (from ear mid-point)

| | |
|---|---|
| Length: | 11 mm |
| Width: | 8 mm |
| Thick: | 6 mm |
| Shape Grade (% rounds): | 40–60 (59% medium round based on Parent Test Data) |
| Pericarp Color: | Colorless |
| Aleurone Color: | Homozygous yellow |
| Endosperm Color: | Yellow |
| Endosperm Type: | Normal starch |
| Gm Wt/100 Seeds (unsized): | 30 gm |

G. Cob:

| | |
|---|---|
| Diameter at mid-point: | 29 mm |
| Strength: | Strong |
| Color: | White |

H. Diseases:

| | |
|---|---|
| Corn Lethal Necrosis (MCMV = Maize Chlorotic Mottle Virus and MDMV = Maize Dwarf Mosaic Virus): | Resistant |
| Maize Dwarf mosaic Complex (MDMV & MCDV = Maize Chlorotic Dwarf Virus): | Susceptible |
| Anthracnose Stalk Rot (*C. graminicola*): | Resistant |
| S. Leaf Blight (*H. maydis*): | Resistant |
| N. Leaf Blight (*H. turcicum*): | Intermediate |
| Carbonum Leaf Blight (*H. carbonum*): | Resistant |
| Eye Spot (*K. zeae*): | Intermdiate |
| Gray Leaf Spot (*C. zeae*): | Susceptible |

TABLE 1-continued

VARIETY DESCRIPTION INFORMATION
INBRED = PHP38

| | |
|---|---|
| Stewart's Wilt (*E. stewartii*): | Resistant |
| Goss's Wilt (*C. nebraskense*): | Resistant |
| Common Smut (*U. maydis*): | Intermediate |
| Head Smut (*S. reiliana*): | Highly Resistant |
| Fusarium Ear Mold (*F. moniliforme*): | Resistant |
| I. Insects: | |
| European Corn Borer-1 Leaf Damage (Preflowering): | Susceptible |
| European Corn Borer-2 (Post-flowering): | Intermediate |
| The above descriptions are based on a scale of 1–9, 1 being highly susceptible, 9 being highly resistant. | |
| S (Susceptible): | Would generally represent a score of 1–3. |
| I (Intermediate): | Would generally represent a score of 4–5. |
| R (Resistant): | Would generally represent a score of 6–7. |
| H (Highly Resistant): | Would generally represent a score of 8–9. |
| | Highly resistant does not imply the inbred is immune. |
| J. Variety Most Closely Resembling: | |
| Character | Inbred |
| Maturity | PHK29 |
| Usage | PHG39 |

*If maximum is greater than 86 degrees fahrenheit, then 86 is used and if minimum is less than 50, then 50 is used. Heat units accumulated daily and can not be less than 0.

Data for Items B, C, D, E, F, and G is based primarily on a maximum of two reps from Johnston, Iowa grown in 1988, plus description information from the maintaining station.

ELECTROPHORESIS RESULTS

Isozyme Genotypes for PHP38

Isozyme data were generated for inbred corn line PHP38 according to the procedures described in Stuber, C. W., Wendel, J. F., Goodman, M. M., and Smith, J. S. C., "Techniques and Scoring Procedures for Starch Gel Electrophoresis of Enzymes from Maize (*Zea mays* L.)", Technical Bulletin No. 286, North Carolina Agricultural Research Service, North Carolina State University, Raleigh, N.C. (1988).

The data in Table 2 compares PHP38 with its parents PHG39 and PHK29.

TABLE 2

ELECTROHPORESIS RESULTS FOR PHP38 AND ITS PARENTS PHG39 AND PHK29

| | | PARENTS | |
|---|---|---|---|
| Loci | PHP38 | PHG39 | PHK29 |
| ACP1 | 4 | 4 | 4 |
| ADH1 | 4 | 4 | 4 |
| CAT3 | 9 | 9 | 9 |
| DIA1 | 8 | 8 | 12 |
| GOT1 | 4 | 4 | 4 |
| GOT2 | 2 | 2 | 4 |
| GOT3 | 4 | 4 | 4 |
| IDH1 | 4 | 4 | 4 |
| IDH2 | 6 | 6 | 4 |
| MDH1 | 6 | 6 | 6 |
| MDH2 | 6 | 6 | 3.5 |
| MDH3 | 16 | 16 | 16 |
| MDH4 | 12 | 12 | 12 |
| MDH5 | 12 | 12 | 12 |
| MMM | 4 | 4 | 4 |
| PGM1 | 9 | 9 | 9 |
| PGM2 | 4 | 4 | 4 |
| PGD1 | 2 | 2 | 3.8 |
| PGD2 | 5 | 5 | 5 |
| PHI1 | 4 | 4 | 4 |

INDUSTRIAL APPLICABILITY

This invention also is directed to methods for producing a corn plant by crossing a first parent corn plant with a second parent corn plant wherein the first or second parent corn plant is an inbred corn plant from the line PHP38. Further, both first and second parent corn plants can come from the inbred corn line PHP38. Thus, any such methods using the inbred corn line PHP38 are part of this invention: selfing, backcrosses, hybrid production, crosses to populations, and the like. All plants produced using inbred corn line PHP38 as a parent are within the scope of this invention. Advantageously, the inbred corn line is used in crosses with other, different, corn inbreds to produce first generation ($F_1$) corn hybrid seeds and plants with superior characteristics.

As used herein, the terms "plant and plant parts" include plant cells, plant protoplasts, plant cell tissue culture from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

Tissue culture of corn is described in European Patent Application, publication 160,390, incorporated herein by reference. Corn tissue culture procedures are also described in Green and Rhodes, "Plant Regeneration in Tissue Culture of Maize," *Maize for Biological Research* (Plant Molecular Biology Association, Charlottesville, Va. 1982, at 367–372).

Thus, another aspect of this invention is to provide cells which upon growth and differentiation produce the inbred line PHP38.

The utility of inbred line PHP38 also extends to crosses with other species. Commonly, suitable species will be of the family Graminaceae, and especially of the genera Zea, Tripsacum, Coix, Schlerachne, Polytoca, Chionachne, and Trilobachne, of the tribe Maydeae. Of these, Zea and Tripsacum, are most preferred. Potentially suitable for crosses with PHP38 may be the various varieties of grain sorghum, *Sorghum bicolor* (L.) Moench.

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide corn starch, corn syrups, and dextrose for food use. Corn oil is recovered from corn germ, which is a by-product of both dry- and wet-milling industries.

Corn, including both grain and non-grain portions of the plant, is also used extensively as livestock feed, primarily for beef cattle, dairy cattle, hogs, and poultry.

Industrial uses of corn are mainly from corn starch from the wet-milling industry and corn flour from the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel and to make charcoal.

The seed of inbred corn line PHP38, the plant produced from the inbred seed, the hybrid corn plant produced from the crossing of the inbred, hybrid seed, and various parts of the hybrid corn plant can be utilized for human food, livestock feed, and as a raw material in industry.

EXAMPLE

INBRED AND HYBRID PERFORMANCE OF PHP38

In the examples that follow the traits and characteristics of inbred corn line PHP38 are given as a line in comparison with its parents and in hybrid combination. The data collected on inbred corn line PHP38 is presented for the key characteristics and traits.

The results in Table 3A compare PHP38 to its PHG39 parent. The results show that PHP38 is significantly higher yielding and has lower grain moisture at maturity than PHG39. PHP38 flowers (GDU SHD and GDU SLK) earlier than PHG39. PHP38 is shorter with lower ear placement than PHG39 and has significantly fewer barren plants. PHP38 has better seedling vigor, lower early stand establishment and cold tolerance than PHG39. PHP38 has a higher test weight and scatter grain score than PHG39. In the areas of disease and insect resistance, PHP38 has better agronomic traits, ear mold, Northern leaf blight, and Stewart's wilt resistance but is more susceptible to first brood European corn borer than PHG39.

Table 3B compares PHP38 with inbred PHK29. PHK29 is the other parent of PHP38. PHP38 is lower yielding but has higher test weight than PHK29. PHP38 is shorter, has lower ear placement, and has fewer barren plants than PHK29. The seedling vigor and early stand establishment of PHP38 is better than PHK29 but has fewer kernels germinate under cold soil conditions. PHP38 flowers (GDU SHD and GDU SLK) earlier than PHK29. Stalk lodging, brittle stalk, and Northern and Southern leaf blight resistance is greater for PHP38 but PHP38 is more susceptible to first brood corn borer than PHK29.

Tables 4–9 compare PHP38 hybrids to Pioneer Brand hybrids 3362, 3467, 3540, 3569, 3379, and 3344, respectively. Each hybrid has a parent in common with the PHP38 hybrid other than PHP38. The hybrids are adapted to much of the same area as the PHP38 hybrids. Table 4 compares a PHP38 hybrid with 3362. The PHP38 hybrid yields significantly more bushels per acre and has a higher test weight than 3362. The PHP38 hybrid has better seedling vigor, is shorter, and ear placement is lower than 3362. Stalk lodging resistance is better and the stay green score of the PHP38 hybrid is higher than 3362.

The results of Table 5, comparing the PHP38 hybrid with 3467, show a number of agronomic differences. The PHP38 hybrid yields less, is taller, and has higher ear placement than 3467. The stalk and root lodging resistance of the PHP38 hybrid is better than 3467.

Table 6 shows that the PHP38 hybrid yields more, has higher test weight, and flowers earlier (GDU SHD) than 3540. Root lodging resistance and the stay green score is lower for the PHP38 hybrid and it has more dropped ears than 3540.

Table 7 shows the results between a PHP38 hybrid and 3569. The PHP38 hybrid is slightly higher yielding, has significantly higher test weight, and more grain moisture at maturity than 3569. The PHP38 hybrid and 3569 have similar plant and ear height but the PHP38 hybrid flowers (GDU SHD) slightly earlier than 3569. Stay green and grain quality are significantly better for the PHP38 hybrid than 3569. Stalk lodging resistance is significantly better for the PHP38 hybrid but it is more prone to root lodging than 3569, and the PHP38 hybrid also shows the potential for ear droppage.

The results in Table 8 show the PHP38 hybrid is significantly lower yielding, has significantly higher test weight, and has significantly more grain harvest moisture than 3379. The PHP38 hybrid is shorter, has slightly lower ear placement, and flowers (GDU SHD) similarly compared to 3379. The PHP38 hybrid has better seedling vigor but a lower early stand than 3379. Stay green and stalk lodging resistance are significantly better for the PHP38 hybrid but root lodging resistance is similar compared to 3379.

Table 9 compares a PHP38 hybrid with 3344. The PHP38 hybrid yields slightly more, has higher test weight, and similar grain moisture at maturity compared to 3344. The PHP38 hybrid and 3344 have similar plant and ear height and flower (GDU SHD) similarly. The PHP38 hybrid has significantly better stay green and seedling vigor than 3344. The PHP38 hybrid has better stalks but is slightly more prone to root lodging than 3344, and the PHP38 hybrid also shows the tendency to drop ears. These results show that PHP38 hybrids offer significant advantage over commercial products that are sold for yield and other important agronomic traits.

TABLE 3A

PAIRED INBRED COMPARISON DATA
VARIETY #1 - PHP38
VARIETY #2 - PHG39

| YEAR | REGION | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS | CLD TST ABS |
|---|---|---|---|---|---|---|---|---|---|---|---|---|---|
| TOTAL SUM | | 1 | 62.5 | 103 | 5.8 | 21.6 | 5.5 | 86.3 | 73.5 | 29.1 | 6.8 | 42.2 | 75.0 |
| | | 2 | 44.5 | 70 | 4.7 | 22.0 | 6.1 | 72.4 | 79.1 | 33.0 | 6.1 | 43.5 | 94.5 |
| | | LOCS | 38 | 38 | 19 | 38 | 13 | 15 | 25 | 25 | 44 | 60 | 2 |
| | | DIFF | 18.0 | 33 | 1.1 | 0.3 | 0.5 | 13.9 | 5.6 | 3.9 | 0.7 | 1.3 | 19.5 |
| | | PROB | .000# | .000# | .018+ | .253 | .089* | .041+ | .000# | .000# | .002# | .009# | .081* |

| YEAR | REGION | VAR # | CLD TST % MN | DRP EAR ABS | TIL LER ABS | GDU SHD ABS | GDU SLK ABS | POL SC ABS | TAS BLS ABS | TAS SZ ABS | TEX EAR ABS | TST WT ABS | GRN QUL ABS | SCT GRN ABS |
|---|---|---|---|---|---|---|---|---|---|---|---|---|---|---|
| TOTAL SUM | | 1 | 93 | 99.4 | 1.1 | 147.1 | 148.9 | 5.0 | 9.0 | 5.5 | 6.9 | 58.1 | 7.1 | 5.9 |
| | | 2 | 117 | 99.7 | 1.5 | 154.8 | 157.2 | 5.3 | 7.0 | 5.8 | 6.3 | 56.5 | 7.0 | 4.7 |
| | | LOCS | 2 | 23 | 19 | 57 | 47 | 15 | 1 | 24 | 10 | 38 | 30 | 15 |
| | | DIFF | 24 | 0.3 | 0.4 | 7.7 | 8.4 | 0.3 | 2.0 | 0.3 | 0.6 | 1.6 | 0.2 | 1.1 |
| | | PROB | .080* | .279 | .587 | .000# | .000# | .262 | | .139 | .239 | .000# | .517 | .002# |

| YEAR | REGION | VAR # | STA GRN ABS | STK LDG ABS | RT LDG ABS | BRT STK ABS | EAR MLD ABS | NLF BLT ABS | SLF BLT ABS | STW WLT ABS | ECB DPE ABS | ECB 1LF ABS | ECB 2SC ABS |
|---|---|---|---|---|---|---|---|---|---|---|---|---|---|
| TOTAL SUM | | 1 | 6.5 | 98.3 | 94.7 | 98.0 | 7.4 | 5.0 | 7.0 | 7.0 | 100.0 | 3.8 | 5.8 |
| | | 2 | 6.6 | 97.5 | 89.2 | 99.0 | 6.6 | 4.0 | 8.0 | 4.0 | 99.6 | 4.4 | 5.3 |
| | | LOCS | 35 | 31 | 16 | 4 | 17 | 1 | 1 | 2 | 2 | 22 | 18 |
| | | DIFF | 0.1 | 0.8 | 5.5 | 1.0 | 0.8 | 1.0 | 1.0 | 3.0 | 0.4 | 0.5 | 0.5 |
| | | PROB | .771 | .127 | .027+ | .391 | .114 | | | .374 | .500 | .056* | .446 |

\* = 10% SIG
+ = 5% SIG
# = 1% SIG

TABLE 3B

PAIRED INBRED COMPARISON DATA
VARIETY #1 - PHP38
VARIETY #2 - PHK29

| YEAR | REGION | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS | CLD TST ABS | CLD TST % MN |
|---|---|---|---|---|---|---|---|---|---|---|---|---|---|---|
| TOTAL SUM | | 1 | 65.1 | 103 | 5.6 | 23.2 | 5.4 | 87.2 | 76.8 | 30.3 | 6.5 | 37.9 | 75.0 | 93 |
| | | 2 | 76.6 | 121 | 5.8 | 23.2 | 5.5 | 85.7 | 80.3 | 32.9 | 5.5 | 37.0 | 80.0 | 99 |
| | | LOCS | 52 | 52 | 23 | 52 | 14 | 16 | 34 | 34 | 63 | 80 | 2 | 2 |
| | | DIFF | 11.5 | 18 | 0.2 | 0.0 | 0.1 | 1.5 | 3.5 | 2.6 | 1.0 | 1.0 | 5.0 | 6 |
| | | PROB | .000# | .000# | .686 | .878 | .612 | .651 | .004# | .006# | .000# | .090* | .344 | .344 |

| YEAR | REGION | VAR # | DRP EAR ABS | TIL LER ABS | GDU SHD ABS | GDU SLK ABS | POL SC ABS | TAS BLS ABS | TAS SZ ABS | TEX EAR ABS | TST WT ABS | GRN QUL ABS | SCT GRN ABS | STA GRN ABS |
|---|---|---|---|---|---|---|---|---|---|---|---|---|---|---|
| TOTAL SUM | | 1 | 99.6 | 0.9 | 146.8 | 148.5 | 5.2 | 9.0 | 5.4 | 7.1 | 57.5 | 6.6 | 5.9 | 6.6 |
| | | 2 | 99.7 | 4.7 | 148.9 | 152.1 | 5.7 | 9.0 | 5.3 | 6.1 | 56.9 | 6.9 | 6.6 | 6.5 |
| | | LOCS | 33 | 21 | 72 | 58 | 19 | 1 | 31 | 12 | 52 | 42 | 18 | 39 |
| | | DIFF | 0.2 | 3.8 | 2.1 | 3.6 | 0.5 | 0.0 | 0.2 | 1.0 | 0.6 | 0.3 | 0.6 | 0.1 |
| | | PROB | .308 | .073* | .000# | .000# | .216 | | .567 | .004# | .002# | .124 | .119 | .795 |

| YEAR | REGION | VAR # | STK LDG ABS | RT LDG ABS | BRT STK ABS | COM RST ABS | EAR MLD ABS | GLF SPT ABS | NLF BLT ABS | SLF BLT ABS | STW WLT ABS | ECB DPE ABS | ECB 1LF ABS | ECB 2SC ABS |
|---|---|---|---|---|---|---|---|---|---|---|---|---|---|---|
| TOTAL SUM | | 1 | 97.7 | 95.9 | 98.9 | 7.0 | 7.6 | 2.5 | 5.0 | 7.0 | 7.0 | 100.0 | 3.9 | 6.0 |
| | | 2 | 90.8 | 98.3 | 96.1 | 7.0 | 7.4 | 3.2 | 3.0 | 3.0 | 8.0 | 100.0 | 4.4 | 5.5 |
| | | LOCS | 42 | 20 | 7 | 1 | 20 | 7 | 1 | 1 | 2 | 2 | 28 | 23 |
| | | DIFF | 6.8 | 2.3 | 2.7 | 0.0 | 0.1 | 0.7 | 2.0 | 4.0 | 1.0 | 0.0 | 0.5 | 0.5 |
| | | PROB | .001# | .391 | .150 | | .839 | .035+ | | | .000# | 1.00 | .036+ | .448 |

\* = 10% SIG

TABLE 3B-continued

PAIRED INBRED COMPARISON DATA
VARIETY #1 - PHP38
VARIETY #2 - PHK29

+ = 5% SIG
# = 1% SIG

TABLE 4

PHP38 HYBRID COMPARED TO PIONEER HYBRID 3362
VARIETY #1 - PHP38 HYBRID
VARIETY #2 - 3362

| YEAR | REGION | VAR # | PRM | SEL IND | BU ACR ABS | BU ACR % MN | MST ABS | GDU SHD ABS | STK LDG ABS | RT LDG ABS | BAR PLT ABS |
|---|---|---|---|---|---|---|---|---|---|---|---|
| TOTAL SUM | | 1 | 119 | 114 | 152.7 | 110 | 21.2 | 136.7 | 94.5 | 94.8 | 97.6 |
| | | 2 | 118 | 105 | 144.7 | 104 | 20.9 | 137.2 | 92.8 | 95.3 | 98.5 |
| | | LOCS | 15 | 15 | 75 | 75 | 75 | 23 | 66 | 40 | 21 |
| | | DIFF | 1 | 9 | 8.0 | 6 | 0.3 | 0.5 | 1.7 | 0.5 | 0.8 |
| | | PROB | .160 | .000# | .000# | .000# | .030+ | .343 | .011+ | .490 | .158 |

| YEAR | REGION | VAR # | STA GRN ABS | TST WTA ABS | COB SC ABS | GRN QUL ABS | SDG VGR ABS | EST CNT ABS | PLT HT ABS | EAR HR ABS | DRP EAR ABS | BRT STK ABS |
|---|---|---|---|---|---|---|---|---|---|---|---|---|
| TOTAL SUM | | 1 | 6.2 | 58.4 | 4.8 | 7.5 | 6.2 | 61.4 | 104.7 | 43.9 | 99.4 | 98.3 |
| | | 2 | 5.6 | 57.2 | 4.5 | 6.7 | 5.4 | 60.8 | 105.4 | 45.8 | 99.5 | 98.9 |
| | | LOCS | 39 | 74 | 6 | 29 | 42 | 45 | 31 | 31 | 49 | 8 |
| | | DIFF | 0.6 | 1.3 | 0.3 | 0.8 | 0.9 | 0.6 | 0.7 | 1.9 | 0.1 | 0.6 |
| | | PROB | .027+ | .000# | .745 | .001# | .000# | .435 | .250 | .014+ | .741 | .165 |

* = 10% SIG
+ = 5% SIG
# = 1% SIG

TABLE 5

PHP38 HYBRID COMPARED TO PIONEER HYBRID 3467
VARIETY #1 - PHP38 HYBRID
VARIETY #2 - 3467

| YEAR | REGION | VAR # | PRM | SEL IND | BU ACR ABS | BU ACR % MN | MST ABS | GDU SHD ABS | STK LDG ABS | RT LDG ABS |
|---|---|---|---|---|---|---|---|---|---|---|
| TOTAL SUM | | 1 | 117 | 91 | 116.5 | 86 | 16.6 | 130.3 | 92.2 | 92.8 |
| | | 2 | 118 | 95 | 129.6 | 97 | 17.1 | 130.0 | 85.7 | 91.0 |
| | | LOCS | 1 | 1 | 6 | 6 | 6 | 2 | 5 | 3 |
| | | DIFF | 1 | 4 | 13.1 | 10 | 0.5 | 0.3 | 6.5 | 1.8 |
| | | PROB | | | .239 | .203 | .325 | .874 | .242 | .707 |

| YEAR | REGION | VAR # | BAR PLT ABS | STA GRN ABS | TST WTA ABS | GRN QUL ABS | SDG VGR ABS | EST CNT ABS | PLT HT ABS | EAR HT ABS | DRP EAR ABS |
|---|---|---|---|---|---|---|---|---|---|---|---|
| TOTAL SUM | | 1 | 96.7 | 4.8 | 59.1 | 5.8 | 3.8 | 44.1 | 109.5 | 48.3 | 99.6 |
| | | 2 | 96.8 | 3.0 | 59.8 | 5.8 | 4.3 | 56.4 | 107.0 | 43.0 | 99.0 |
| | | LOCS | 1 | 2 | 6 | 6 | 2 | 4 | 2 | 2 | 5 |
| | | DIFF | 0.1 | 1.8 | 0.6 | 0.0 | 0.5 | 12.3 | 2.5 | 5.3 | 0.6 |
| | | PROB | | .395 | .260 | .000 | .500 | .169 | .344 | .030+ | .309 |

* = 10% SIG
+ = 5% SIG
# = 1% SIG

TABLE 6

PHP38 HYBRID COMPARED TO PIONEER HYBRID 3540
VARIETY #1 - PHP38 HYBRID
VARIETY #2 - 3540

| YEAR | REGION | VAR # | PRM | SEL IND | BU ACR ABS | BU ACR % MN | MST ABS | GDU SHD ABS | STK LDG ABS | RT LDG ABS | BAR PLT ABS |
|---|---|---|---|---|---|---|---|---|---|---|---|
| TOTAL SUM | | 1 | 110 | 97 | 123.1 | 94 | 19.2 | 140.1 | 93.4 | 94.0 | 92.0 |
| | | 2 | 110 | 94 | 120.2 | 93 | 19.3 | 142.4 | 93.1 | 97.0 | 87.5 |
| | | LOCS | 8 | 8 | 38 | 38 | 43 | 13 | 39 | 10 | 2 |
| | | DIFF | 0 | 3 | 2.9 | 1 | 0.1 | 2.2 | 0.3 | 3.0 | 4.5 |
| | | PROB | .848 | .232 | .156 | .362 | .536 | .048+ | .848 | .332 | .295 |

| YEAR | REGION | VAR # | STA GRN ABS | TST WTA ABS | COB SC ABS | GRN QUL ABS | SDG VGR ABS | EST CNT ABS | PLT HT ABS | EAR HT ABS | DRP EAR ABS |
|---|---|---|---|---|---|---|---|---|---|---|---|
| TOTAL SUM | | 1 | 5.0 | 58.6 | 7.2 | 7.5 | 6.3 | 53.0 | 86.0 | 39.6 | 98.9 |
| | | 2 | 5.4 | 57.7 | 7.2 | 7.0 | 6.1 | 52.1 | 88.0 | 40.2 | 99.6 |
| | | LOCS | 27 | 39 | 3 | 39 | 24 | 33 | 21 | 21 | 36 |
| | | DIFF | 0.4 | 0.8 | 0.0 | 0.4 | 0.2 | 0.9 | 2.1 | 0.7 | 0.7 |
| | | PROB | .062* | .000# | .000 | .038+ | .553 | .311 | .014+ | .241 | .041+ |

\* = 10% SIG
+ = 5% SIG
# = 1% SIG

TABLE 7

PHP38 HYBRID COMPARED TO PIONEER HYBRID 3569
VARIETY #1 - PHP38 HYBRID
VARIETY #2 - 3569

| YEAR | REGION | VAR # | PRM | SEL IND | BU ACR ABS | BU ACR % MN | MST ABS | GDU SHD ABS | STK LDG ABS | RT LDG ABS | BAR PLT ABS |
|---|---|---|---|---|---|---|---|---|---|---|---|
| TOTAL SUM | | 1 | 109 | 102 | 137.9 | 99 | 18.8 | 139.3 | 95.0 | 95.0 | 91.0 |
| | | 2 | 108 | 99 | 136.0 | 99 | 18.5 | 140.0 | 85.4 | 98.0 | 92.7 |
| | | LOCS | 12 | 12 | 52 | 52 | 55 | 15 | 50 | 17 | 9 |
| | | DIFF | 1 | 3 | 1.9 | 1 | 0.3 | 0.6 | 9.6 | 3.0 | 1.6 |
| | | PROB | .114 | .366 | .404 | .748 | .024+ | .346 | .000# | .201 | .299 |

| YEAR | REGION | VAR # | STA GRN ABS | TST WTA ABS | COB SC ABS | GRN QUL ABS | SDG VGR ABS | EST CNT ABS | PLT HT ABS | EAR HT ABS | DRP EAR ABS |
|---|---|---|---|---|---|---|---|---|---|---|---|
| TOTAL SUM | | 1 | 4.9 | 58.9 | 7.1 | 7.5 | 6.7 | 59.5 | 91.8 | 42.2 | 98.7 |
| | | 2 | 3.2 | 57.3 | 6.9 | 6.7 | 6.9 | 61.9 | 91.7 | 42.3 | 99.4 |
| | | LOCS | 24 | 52 | 4 | 31 | 21 | 36 | 25 | 25 | 41 |
| | | DIFF | 1.7 | 1.7 | 0.3 | 0.8 | 0.2 | 2.4 | 0.1 | 0.2 | 0.7 |
| | | PROB | .000# | .000# | .391 | .008# | .455 | .016+ | .861 | .823 | .035+ |

\* = 10% SIG
+ = 5% SIG
# = 1% SIG

TABLE 8

PHP38 HYBRID COMPARED TO PIONEER HYBRID 3379
VARIETY #1 - PHP38 HYBRID
VARIETY #2 - 3379

| YEAR | REGION | VAR # | PRM | SEL IND | BU ACR ABS | BU ACR % MN | MST ABS | GDU SHD ABS | STK LDG ABS | RT LDG ABS | BAR PLT ABS |
|---|---|---|---|---|---|---|---|---|---|---|---|
| TOTAL SUM | | 1 | 124 | 102 | 140.5 | 99 | 21.0 | 142.3 | 98.2 | 94.8 | 94.1 |
| | | 2 | 121 | 110 | 148.3 | 106 | 19.5 | 141.7 | 94.7 | 94.4 | 94.5 |
| | | LOCS | 12 | 12 | 58 | 58 | 59 | 12 | 53 | 32 | 16 |
| | | DIFF | 3 | 8 | 7.8 | 7 | 1.5 | 0.6 | 3.4 | 0.4 | 0.4 |

TABLE 8-continued

PHP38 HYBRID COMPARED TO PIONEER HYBRID 3379
VARIETY #1 - PHP38 HYBRID
VARIETY #2 - 3379

| | | | PROB | .006# | .093* | .004# | .004# | .000# | .395 | .013+ | .637 | .556 |
|---|---|---|---|---|---|---|---|---|---|---|---|---|
| YEAR | REGION | VAR # | | STA GRN ABS | TST WTA ABS | COB SC ABS | GRN QUL ABS | SDG VGR ABS | EST CNT ABS | PLT HT ABS | EAR HT ABS | DRP EAR ABS | BRT STK ABS |
| TOTAL SUM | | 1 | | 6.7 | 58.0 | 6.9 | 7.9 | 6.2 | 60.7 | 99.5 | 42.9 | 99.7 | 95.5 |
| | | 2 | | 6.1 | 57.8 | 7.5 | 7.8 | 5.6 | 64.0 | 102.3 | 43.5 | 99.6 | 95.3 |
| | | LOCS | | 34 | 58 | 4 | 25 | 24 | 40 | 27 | 27 | 32 | 6 |
| | | DIFF | | 0.5 | 0.3 | 0.5 | 0.1 | 0.5 | 3.4 | 2.8 | 0.6 | 0.0 | 0.1 |
| | | PROB | | .051* | .035+ | .435 | .648 | .049+ | .000# | .007# | .331 | .773 | .874 |

\* = 10% SIG
+ = 5% SIG
# = 1% SIG

TABLE 9

PHP38 HYBRID COMPARED TO PIONEER HYBRID 3344
VARIETY #1 - PHP38 HYBRID
VARIETY #2 - 3344

| YEAR | REGION | VAR # | PRM | SEL IND | BU ACR ABS | BU ACR % MN | MST ABS | GDU SHD ABS | STK LDG ABS | RT LDG ABS | BAR PLT ABS |
|---|---|---|---|---|---|---|---|---|---|---|---|
| TOTAL SUM | | 1 | 123 | 106 | 145.3 | 104 | 20.8 | 145.5 | 96.0 | 92.1 | 91.5 |
| | | 2 | 122 | 106 | 144.7 | 104 | 20.6 | 144.9 | 91.2 | 93.3 | 94.5 |
| | | LOCS | 13 | 14 | 77 | 77 | 77 | 16 | 75 | 30 | 13 |
| | | DIFF | 1 | 1 | 0.6 | 0 | 0.2 | 0.6 | 4.8 | 1.2 | 3.0 |
| | | PROB | .140 | .728 | .758 | .786 | .156 | .273 | .000# | .497 | .260 |

| YEAR | REGION | VAR # | STA GRN ABS | TST WTA ABS | COB SC ABS | GRN QUL ABS | SDG VGR ABS | EST CNT ABS | PLT HT ABS | EAR HT ABS | DRP EAR ABS |
|---|---|---|---|---|---|---|---|---|---|---|---|
| TOTAL SUM | | 1 | 5.8 | 57.2 | 5.4 | 6.9 | 6.6 | 61.5 | 100.4 | 42.3 | 99.0 |
| | | 2 | 5.1 | 55.8 | 5.8 | 6.2 | 5.7 | 62.0 | 100.3 | 42.1 | 99.8 |
| | | LOCS | 43 | 77 | 6 | 42 | 26 | 47 | 29 | 29 | 38 |
| | | DIFF | 0.7 | 1.4 | 0.4 | 0.7 | 0.8 | 0.5 | 0.1 | 0.2 | 0.7 |
| | | PROB | .020+ | .000# | .338 | .004# | .003# | .365 | .878 | .630 | .007# |

\* = 10% SIG
+ = 5% SIG
# = 1% SIG

Deposits

Applicants have made available to the public without restriction a deposit of at least 2500 seeds of inbred PHP38 with the American Type Culture Collection (ATCC), Rockville, Md. 20852 U.S.A., ATCC Deposit No. 75612. The seeds were deposited with the ATCC on Nov. 9, 1993, and are taken from the same deposit maintained by Pioneer Hi-Bred International Inc., 700 Capital Square, 400 Locust Street, Des Moines, Iowa 50309 since prior to the filing date of this application. This deposit of the Inbred Corn Line PHP38 will be maintained without restriction in the ATCC depository, which is a public depository, for a period of 30 years, or 5 years after the most recent request, or for the effective life of the patent, whichever is longer, and will be replaced if it becomes nonviable during that period.

What is claimed is:

1. Inbred corn seed designated PHP38, having ATCC accession No. 75612.
2. A corn plant produced by the seed of claim 1.
3. A tissue culture of regenerable cells of the plant of claim 2.
4. Tissue culture according to claim 3 comprising regenerable cells of a plant part selected from meristematic tissue, anthers, leaves, embryos, pollen, and protoplasts thereof.
5. A corn plant regenerated from the regenerable cells of a tissue culture of claim 4, said plant possessing all the physiological and morphological characteristics of the inbred corn plant designated PHP38.
6. An inbred corn plant having all the physiological and morphological characteristics of the plant of claim 2.

* * * * *